US00PP19556P2

(12) United States Plant Patent
Zary

(10) Patent No.: US PP19,556 P2
(45) Date of Patent: Dec. 9, 2008

(54) HYBRID TEA ROSE PLANT NAMED 'JACORMAG'

(50) Latin Name: *Rosa hybrida*
Varietal Denomination: JACormag

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,258

(22) Filed: Nov. 28, 2007

(51) Int. Cl.
*A01H 5/00* (2006.01)

(52) U.S. Cl. ..... Plt./136

(58) Field of Classification Search ..... Plt./136
See application file for complete search history.

*Primary Examiner*—Annette H Para
(74) *Attorney, Agent, or Firm*—Klarquist Sparkman, LLP

(57) ABSTRACT

Hybrid tea rose plant named 'JACormag' having very large flowers; long cutting stems; vigorous, upright, well branched growth; and the ability to propagate well from softwood cuttings.

1 Drawing Sheet

Genus and species: *Rosa hybrida.*
Variety denomination: 'JACormag'.

ORIGIN OF THE INVENTION

The present invention relates to a new and distinct variety of a hybrid tea rose plant named 'JACormag' which was originated by me by crossing the variety 'JACmag' (U.S. Plant Pat. No. 3,998, seed parent) with an unnamed Red Hybrid Tea rose (not patented, pollen parent). The pollen parent is a cross between two unnamed red hybrid tea rose varieties.

BACKGROUND OF THE INVENTION

The primary objective of this breeding was to produce a new hybrid tea rose variety having the large flower size and vigorous plant of the female (seed) parent combined with the long stems and own root vigor of the unnamed red hybrid tea male (pollen) parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very large flower.
2. Vigorous, upright, well branched growth.
3. Propagates well from softwood cuttings.
4. Long cutting stems.

Asexual reproduction of this new variety by cuttings, as performed at Wasco, Calif., shows that the foregoing characteristics and distinctions come true to form and are established and transmitted through succeeding propagations.

Comparison with Parents

'JACormag' differs from 'JACmag' in flower color (apricot to ivory pink for 'JACmag' versus orange-red for 'JACormag'). 'JACormag' differs from the unnamed pollen parent in flower color (orange-red for 'JACormag' versus red for the pollen parent).

Comparison with Similar Variety

The closest variety is believed to be 'JACirst' (U.S. Plant Pat. No. 10,230). 'JACormag' differs from 'JACirst' in flower color (coral orange for 'JACirst' versus orange-red for 'JACormag').

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart © 2001, except where ordinary dictionary significance of color is indicated.

Parentage:
*Seed parent.*—'JACmag' (U.S. Plant Pat. No. 3,998).
*Pollen parent.*—Unnamed Red Hybrid Tea (not patented); the pollen parent is a cross, unnamed red hybrid tea×unnamed red hybrid tea.

FLOWER

Observations of the new variety were made from January 2005 to November 2007. The description below is taken from plants at three years of age, growing in a garden environment at Somis, Calif.

Blooming habit: Continuous.
Bud:
*Size.*—About 40 mm long and 30 mm in diameter when the petals start to unfurl.

*Form.*—The bud form is long, pointed ovoid.

*Color.*—When sepals first divide, bud color is Red Group 41C. When half blown, the upper sides of the petals are Red Group 41C in center of the petals and Red Group 41B on the edges and the lower sides of the petals are Red Group 41D.

*Sepals.*—Color: Upper surface: Green Group 138C. Lower surface: Yellow-Green Group 146B Sometimes with a blush of Greyed-Red Group 178B. Length: 30 mm. Width: 14 mm. Shape: Subulate. Surface: Hoary. There are three lightly appendaged sepals. There are two unappendaged sepals with hairy edges.

*Receptacle.*—Color: Yellow-Green Group 146B. Shape: Funnel. Size: Large, about 15 mm long×15 mm in width. Surface: Smooth.

*Peduncle.*—Length: Short, averaging about 45–50 mm. Surface: Smooth. Color: Yellow-Green Group 146B. Strength: Stiff, erect, heavy.

Bloom:

*Size.*—Large. Average open diameter is about 12–13 cm.

*Borne.*—Singly.

*Stems.*—Strength: Strong. Average length is about 40–50 cm with a diameter of 7–8 mm.

*Form.*—When first open: High centered. Permanence: Flattens, all petals curl.

*Petalage.*—Number of petals under normal conditions: 30.

*Color.*—The upper sides of the petals are Red Group 41B on petal edges and Red Group 41C over the rest of the petal. The reverse sides of the petals are Red Group 41D. The base of the petals has a 5 mm×5 mm Yellow Group 8B color spot. The major color on the upper sides is Red Group 41C.

*Variegations.*—Occasional White Group 155C streak on the guard petal.

*Discoloration.*—The general tonality at the end of the first day: No change. At the end of the third day: No change. Further aging: General increase in color to Red group 41A on petal edges by day 5.

*Fragrance.*—Moderate, spicy.

Petals:

*Thickness.*—Leathery.

*Surface texture.*—Smooth.

*Shape.*—Round.

*Margin.*—Entire.

*Apex shape.*—Rounded.

*Base shape.*—Rounded.

*Form.*—Tips slightly recurved.

*Arrangement.*—Imbricated.

*Petaloids.*—Number: 3–7. Size: Range from 3 to 15 mm long and 1 to 8 mm wide. Color: Red Group 41C.

*Persistence.*—Petals drop off cleanly before drying.

*Lastingness.*—On the plant: Long (about 6–7 days). As a cut flower: Long (about 8–9 days).

Reproductive parts:

*Stamens.*—Number: 50 to 60. Length: 7 mm. Anthers: Length: 3 mm. Color: Yellow-Orange Group 18B. Arrangement: Regular around styles. Filaments: Color: Red Group 45D. Length: 3–4 mm. Pollen: Color: Greyed-Orange Group 165B.

*Pistils.*—Number: 65 to 70. Length: 5 mm. Styles: Color: Red Group 45D. Length: 4 mm. Stigmas: Color: Yellow-White Group 158C. Length: 1 mm.

*Hips.*—None observed.

PLANT

*Form.*—Bush.

*Growth.*—Very vigorous, upright, branching.

*Age to maturity.*—Two years.

*Mature plant.*—Height: 160 to 180 cm. Width: 110 to 130 cm.

*Rootstock.*—Own root.

Foliage: Number of leaflets on normal mid-stem leaves.—5.

*Size.*—Large. About 15 cm long×12 cm wide.

*Quantity.*—Abundant.

*Color.*—New foliage: Upper side: Greyed-Red Group 178A. Lower side: Greyed-Red Group 178A. Old foliage: Upper side: Green Group 139A. Lower side: Yellow-Green Group 147B.

Leaflets:

*Size.*—About 6 cm long×4 cm wide.

*Shape.*—Oval.

*Base shape.*—Rounded.

*Apex shape.*—Acuminate.

*Texture.*—Leathery.

*Edge.*—Serrated.

*Serrations.*—Single.

*Petiole.*—Color: Yellow-Green Group 146C.

*Petiole rachis.*—Color: Yellow-Green Group 146C. Both petiole and petiole rachis can have Greyed-Red Group 178B coloration if exposed to bright sunlight. Underside: Smooth with an occasional prickle.

*Auricles.*—None observed.

*Stipules.*—Length: 15 mm, smooth.

*Disease resistance.*—Resistant to rust, susceptible to blackspot and mildew under normal growing conditions.

*Pest resistance.*—None observed.

*Vein color.*—Yellow-Green Group 147B.

*Venation pattern.*—Reticulate.

Wood:

*New wood.*—Color: Yellow-Green Group 146C. Bark: Smooth.

*Old wood.*—Color: Yellow-Green Group 146B. Bark: Smooth.

Prickles:

*Quantity.*—Ordinary, on main canes from base: 9 per 15 cm of cane. Ordinary, on laterals from main canes.

*Form.*—Hooked downward.

*Length.*—5–6 mm.

*Color when young.*—Greyed-Red Group 178B.

*Color when mature.*—Greyed-Orange Group 177B.

Small prickles:

*Quantity.*—On main stalks: None observed. On laterals: None observed.

Winter hardiness: Hardy to Zone 5.

I claim:

1. A new and distinct variety of hybrid tea rose plant, substantially as herein shown and described, characterized particularly by very large flowers; long cutting stems; vigorous, upright, well branched growth; and the ability to propagate and grow well from softwood cuttings.

* * * * *

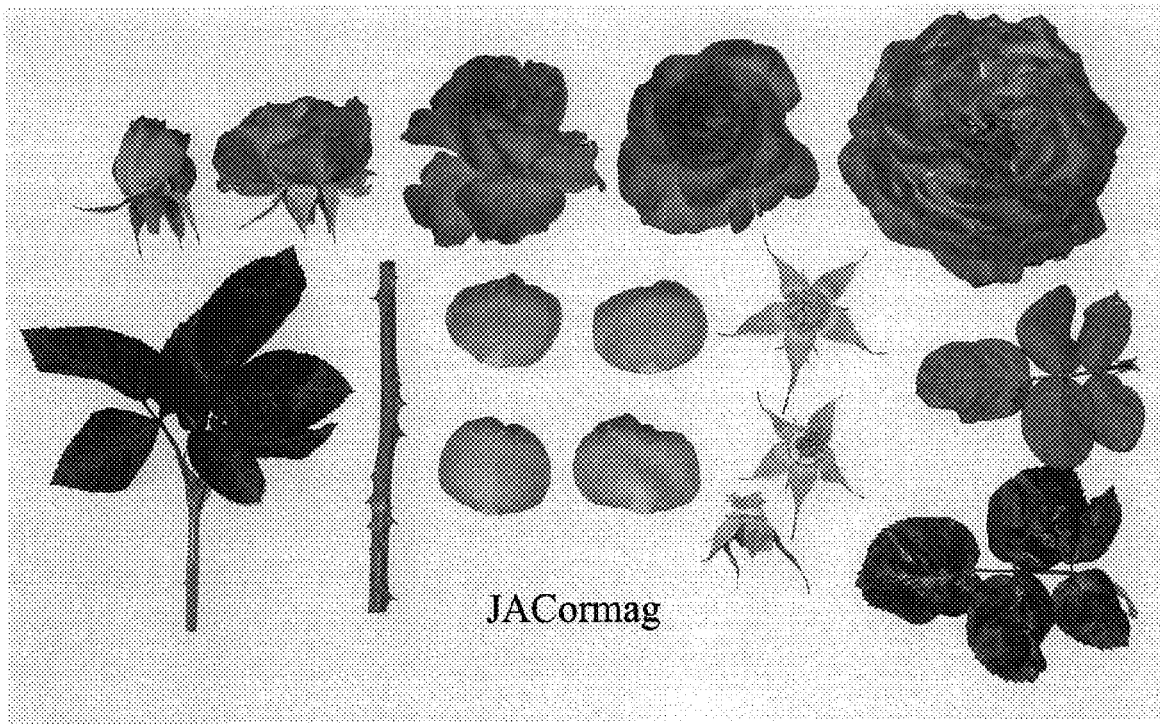
JACormag